(12) United States Patent
Westerkamp

(10) Patent No.: US 11,331,444 B2
(45) Date of Patent: May 17, 2022

(54) APPARATUS FOR RESPIRATING OF PATIENTS

(71) Applicant: ALCMAIR PARTNERS BV, Alkmaar (NL)

(72) Inventor: Bart Westerkamp, Alkmaar (NL)

(73) Assignee: LÖWENSTEIN MEDICAL TECHNOLOGY SA, Luxembourg (LU)

(*) Notice: Subject to any disclaimer, the term of this patent is extended or adjusted under 35 U.S.C. 154(b) by 14 days.

(21) Appl. No.: 15/101,588

(22) PCT Filed: Dec. 5, 2014

(86) PCT No.: PCT/NL2014/000047
§ 371 (c)(1),
(2) Date: Jun. 3, 2016

(87) PCT Pub. No.: WO2015/084159
PCT Pub. Date: Jun. 11, 2015

(65) Prior Publication Data
US 2018/0161533 A1    Jun. 14, 2018

(30) Foreign Application Priority Data

Dec. 6, 2013 (NL) ...................... 1040531

(51) Int. Cl.
*A61M 16/08* (2006.01)
*A61M 16/22* (2006.01)
(Continued)

(52) U.S. Cl.
CPC ........ *A61M 16/01* (2013.01); *A61M 16/0891* (2014.02); *A61M 16/20* (2013.01);
(Continued)

(58) Field of Classification Search
CPC ..... A61M 16/0057–0081; A61M 16/08–0891; F04B 31/00; F04B 9/1222; F04B 17/00
See application file for complete search history.

(56) References Cited

U.S. PATENT DOCUMENTS 3,489,335 A * 1/1970 Mark ...................... F04B 31/00
417/328
4,493,614 A * 1/1985 Chu .................. A61M 16/0072
128/204.21
(Continued)

*Primary Examiner* — Rachel T Sippel
(74) *Attorney, Agent, or Firm* — Egbert, McDaniel & Swartz, PLLC

(57) ABSTRACT

Apparatus for the respiration of patients with means for the circulation in one direction of respiratory gas, with a connection for the patient and with further connections for the supply and discharge of the various components of the gas, whereby the device is provided with means by which the pressure in the line system can be varied according to a certain respiratory pattern, with a primary part that is connected to means for the generating of a work fluidum, the varying pressure of which can establish the varying of the pressure in the line system, and with a secondary part that is part of or is connected to the line system, whereby a cylinder is provided which is divided in a part that connects to the primary part and a part that connects to the secondary part by a disc that is movable relative to the inner wall thereof.

10 Claims, 1 Drawing Sheet

(51) Int. Cl.
  *A61M 16/00* (2006.01)
  *A61M 16/01* (2006.01)
  *A61M 16/20* (2006.01)

(52) U.S. Cl.
  CPC ......... *A61M 16/22* (2013.01); *A61M 16/0057* (2013.01); *A61M 2016/0033* (2013.01); *A61M 2209/10* (2013.01); *A61M 2230/43* (2013.01)

(56) References Cited

U.S. PATENT DOCUMENTS

| | | | | |
|---|---|---|---|---|
| 5,092,743 | A * | 3/1992 | Dietrich | F04B 9/1222 417/126 |
| 5,628,305 | A * | 5/1997 | Melker | A61M 16/0048 128/202.29 |
| 5,807,083 | A * | 9/1998 | Tomoiu | F04B 9/107 417/392 |
| 6,213,120 | B1 * | 4/2001 | Block | A61M 16/0075 128/204.21 |
| 2002/0040715 | A1 * | 4/2002 | Barrett | F04B 25/00 128/205.18 |
| 2015/0250960 | A1 * | 9/2015 | Broberg | A61M 16/01 128/203.12 |

* cited by examiner

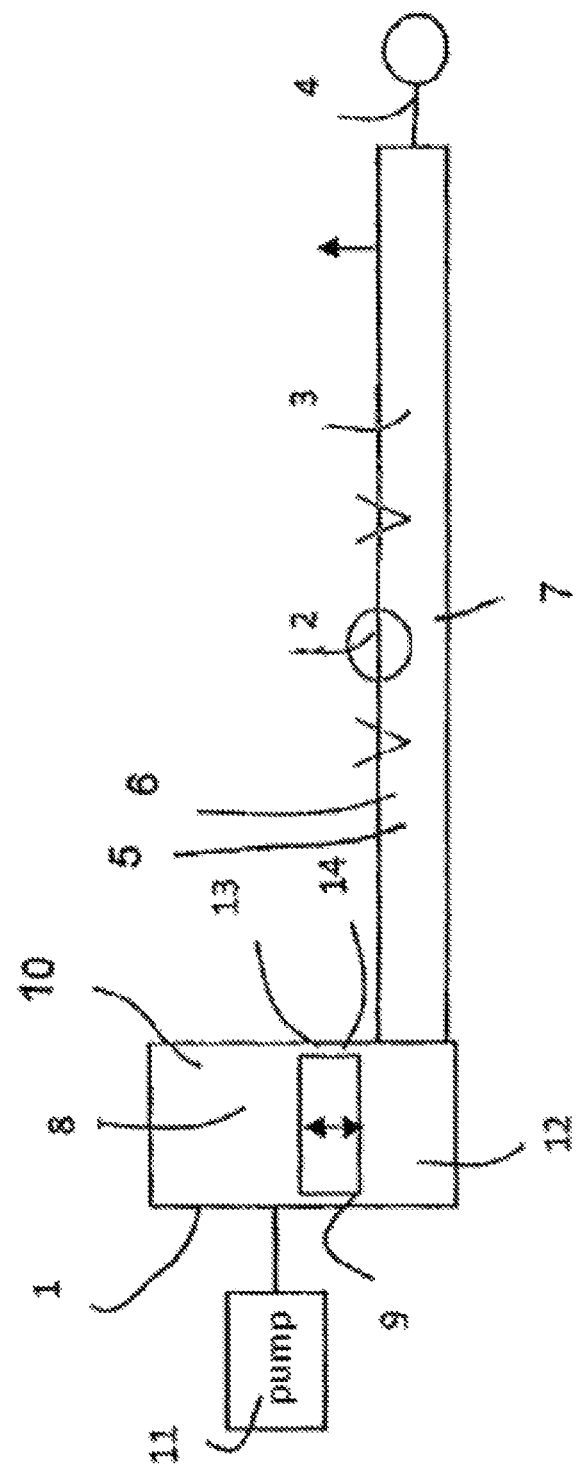

APPARATUS FOR RESPIRATING OF PATIENTS

The present invention relates to an apparatus for the respiration of patients, more particularly for anaesthesia and the use in an intensive care unit, which apparatus is provided with means for the circulation in one direction of respiratory gas, anaesthetic gas or therapeutic gas in a line system, that is provided with a connection for the patient and with further connections for the supply of the various components of the gas and with means for the withdrawal of the carbon dioxide exhaled by the patient in the line system, whereby the apparatus is provided with means by which the pressure in the line system can be varied in accordance with a certain respiratory pattern, and whereby the means comprise a primary part, that is connected to means for the generating of a work fluidum, the varying pressure of which can effect the varying of the pressure in the line system, and comprise a secondary part, that is part of or is connected to the line system.

In a known apparatus described in the Dutch publication 8301191 the means for the varying in accordance with a certain respiratory pattern of the pressure in the line system are formed by a pump with behind it a volume displacement meter in the form of a cylinder in which a bell-shaped piston with the interposition of a roll membrane is to and fro movable. This known apparatus has the drawback that it is complicated. Furthermore the cleaning of the pump is not well possible.

From the European patent application EP-A 0281 180 is known an apparatus with a pump and a number of parallel switched, simultaneously operatable, pump chambers which are divided by a pump membrane into a primary part, that is connected to means for the generating of a work fluidum, the varying pressure of which can effect the varying of the pressure in the line system, and a secondary part, that is part of or is connected to the line system.

This known apparatus has the drawback that it is not well possible to adapt the volume of the primary part or that of the secondary part, onto which the patient is connected, during use by means of the switching on or off of the chambers. Furthermore in this known apparatus the chambers cannot be opened for cleaning thereof.

The apparatus according to the invention aims to obviate this drawback of the known apparatuses and to provide an apparatus, by means of which it is possible to regulate the compressible volume in the closed line system optimally, while further the cleaning can be performed in a simple manner.

The apparatus according to the invention thereto is characterized, in that a cylinder is provided which is divided in a part that connects to the primary part and a part that connects to the secondary part by a disc that is movable to and fro relative to the inner wall thereof.

According to a characteristic of the apparatus according to the invention the surface of the wall of the disc lies close against the surface of the inner wall of the cylinder, such that the disc is sealingly movable in the cylinder.

According to a further characteristic of the apparatus according to the invention the cylinder and the disc are completely or in part made from a ceramic material, whereby this, according to another characteristic of the apparatus according to the invention, is the same ceramic material and, according to yet a further characteristic of the apparatus according to the invention, consists of aluminium oxide. Possibly this is provided with a plastic coating, for instance Teflon, in order to improve the sliding properties and to reduce the resistance further, which is advantageous for the patient who is breathing spontaneously, as well as the patient who is being ventilated.

According to another characteristic of the apparatus according to the invention the work fluidum is formed by a gas and the means for the varying of the pressure are formed by a flow pump or these are formed by a compressed air device, which is connected through one or more valves to the lining system.

According to the invention the combination of the cylinder and the disc is formed and made, completely or in part, from a ceramic material, whereby the surface of the wall of the disc close-fittingly abuts the surface of the inner wall of the cylinder, in such way that the disc in the cylinder is sealingly to and fro movable, without any further measure, such as the placement of a means, such as for instance a membrane, in the space in between the disc and the cylinder, being required. With the, by means of a flow pump, bringing about of a varying pressure the reciprocating movement of the disc in the cylinder can be brought about in a very accurate manner and thereby an accurate regulation of the pressure in the closed line system, towards the patient, can be achieved. Because there is no connection of the disc with the cylinder this is demountable and the cleaning can take place in a simple manner.

According to another characteristic of the apparatus according to the invention the cylinder is arranged vertically and the disc therein is up and down movable.

According to another characteristic of the apparatus according to the invention the cylinder is arranged horizontally and the disc therein is to and fro movable.

According to yet another characteristic of the apparatus according to the invention the part in the cylinder underneath the disc forms the secondary part and the part in the cylinder above the disc forms the primary part.

Further characteristics and details of the invention will be described with reference to the drawing of an example of an embodiment of the invention.

The FIGURE shows schematically an example of an embodiment of the apparatus according to the invention.

As shown in the FIGURE, the apparatus 1 is provided with a circulation pump 2 for the circulating in one direction of the respiratory gas, anaesthetic gas or therapeutic gas in a closed line system 3, which is provided with a connection 4 for the patient and with further connections 5, 6 for the supply of the various components of the gas, and with an absorber device 7 for the withdrawing of the carbon dioxide exhaled by the patient in the line system 3. In this example of an embodiment the apparatus is provided with a vertically arranged cylinder 8 containing a disc 9 which is freely up and down movable therein, which divides the cylinder in a primary part 10, that is connected, in this embodiment, to a further circulation pump 11, by means of which the pressure of a work fluidum in the primary part 10 can be varied, and a secondary part 12 that is part of or is connected to the line system 3. With the varying of the pressure of the work fluidum in the primary part 10 an upward and downward movement of the disc 9 in the cylinder 8 is effected, and by which the pressure in the line system 3 can be varied according to a certain respiratory pattern. The wall 13 of the disc 9 has a certain height. In the example shown this has a height between 30 mm to 35 mm. The diameter of the disc in the shown embodiment is 133 mm and the stroke 200 mm. The surface of the wall 13 of the disc 9 lies along this height close against the surface of the inner wall 14 of the cylinder, such that the disc is sealingly movable in the cylinder.

The cylinder and the disc are manufactured from the same material, preferably a ceramic material, for instance aluminium oxide. Or both of a same composition, for example aluminium with a ceramic layer of aluminium oxide.

The apparatus further is provided with means, not shown in the drawing, by which the path of movement of the disc upwards, towards the primary part, and downwards towards the secondary part, can be limited in an end position. By means of this the total volume of the primary and the secondary part can be adapted, that is to say, can be decreased or increased. Further the device is provided with means, not shown in the drawing, by which the end positions are adjustable. Further a contactless reader can be provided by means of which the position of the disc can be determined (for example ultrasonically or optically).

By this it is achieved that an optimal regulation is possible of the volumes of the primary and secondary parts, more particularly the optimal regulation of the compressible volume in the closed line system, towards the patient.

The invention claimed is:

1. An apparatus for respirating a patient with a gas, the apparatus comprising:
    a closed line system having a gas flow passageway;
    a circulation pump cooperative with said closed line system so as to circulate the gas in only one direction in the gas flow passageway;
    a first connector connected to said closed line system, said first connector adapted to connect to a patient;
    a second connector connected to said closed line system at a location away from said first connector, said second connector adapted to connect to a supply of the gas;
    a carbon dioxide withdrawal device cooperative with said closed line system and adapted to withdraw carbon dioxide exhaled by the patient;
    a pressure variance device cooperative with said closed line system so as to vary a pressure of the gas in the gas flow passageway in accordance with a desired respiratory pattern, said pressure variance device having a first part connected to a supply of a work fluid that acts on the pressure variance device so as to vary the pressure of the gas in the line system, said pressure variance device having a second part that is at least partially connected to the line system, said pressure variance device comprising a cylinder having the first part and the second part therein; and
    a disc separating said first part and said second part of said pressure variance device from each other, said disc being movable to-and-fro within said cylinder along an inner wall of said cylinder without any mechanical connection being present between said disc and said pressure variance device nor any components comprising said pressure variance device.

2. The apparatus of claim 1, said disc having an outer periphery adjacent the inner wall of said cylinder.

3. The apparatus of claim 1, wherein said cylinder and said disc are at least partially formed of a ceramic material.

4. The apparatus of claim 3, wherein the ceramic material contains aluminum oxide.

5. The apparatus of claim 3, wherein said cylinder and said disc have a Teflon coating.

6. The apparatus of claim 1, wherein said cylinder is oriented vertically, the to-and-fro movement being an upward-and-downward movement.

7. The apparatus of claim 1, wherein said cylinder is oriented horizontally, the to-and-fro movement being an end-to-end movement.

8. The apparatus of claim 1, wherein the first part is a volume above said disc and the second part is a volume below said disc.

9. The apparatus of claim 1, wherein the work fluid is gaseous, said pressure variance device having a flow pump that directs the work fluid into the first part of said pressure variance device.

10. The apparatus of claim 1, wherein the work fluid is gaseous, wherein said pressure variance device has a compressed air supply connected to said closed line system.

* * * * *